(12) United States Patent
Nik-Zainal et al.

(10) Patent No.: US 11,929,144 B2
(45) Date of Patent: Mar. 12, 2024

(54) METHOD OF DETECTING A MUTATIONAL SIGNATURE IN A SAMPLE

(71) Applicant: Genome Research Limited, Hinxton (GB)

(72) Inventors: Serena Nik-Zainal, Hinxton (GB); Mike Stratton, Hinxton (GB); Dominik Glodzik, Hinxton (GB)

(73) Assignee: Genome Research Limited, Hinxton (GB)

( * ) Notice: Subject to any disclaimer, the term of this patent is extended or adjusted under 35 U.S.C. 154(b) by 981 days.

(21) Appl. No.: 16/096,803

(22) PCT Filed: Apr. 28, 2017

(86) PCT No.: PCT/EP2017/060279
§ 371 (c)(1),
(2) Date: Oct. 26, 2018

(87) PCT Pub. No.: WO2017/191068
PCT Pub. Date: Nov. 9, 2017

(65) Prior Publication Data
US 2020/0126635 A1 Apr. 23, 2020

(30) Foreign Application Priority Data
May 1, 2016 (GB) .................................. 1607628

(51) Int. Cl.
*G16B 20/20* (2019.01)
*G16B 20/00* (2019.01)
(Continued)

(52) U.S. Cl.
CPC ............. *G16B 20/20* (2019.02); *G16B 20/10* (2019.02); *G16B 40/00* (2019.02); *G16B 40/30* (2019.02); *G16B 20/00* (2019.02)

(58) Field of Classification Search
CPC ........ G16B 40/00; G16B 20/00; G16B 20/20; G16B 40/30
(Continued)

(56) References Cited

U.S. PATENT DOCUMENTS

| 7,097,977 B1 | 8/2006 | Takeda et al. |
| 2012/0035244 A1 | 2/2012 | Chinnaiyan et al. |

(Continued)

FOREIGN PATENT DOCUMENTS

| CN | 1976711 A | 6/2007 |
| CN | 101490553 A | 7/2009 |

(Continued)

OTHER PUBLICATIONS

Nicola Waddell, Marina Pajic, Ann-Marie Patch, David K. Chang et al. Whole genomes redefine the mutational landscape of pancreatic cancer, Nature, 518, pp. 495-501, 2015 (7 pages) (Year: 2015).*

(Continued)

*Primary Examiner* — Russell S Negin
*Assistant Examiner* — Guozhen Liu
(74) *Attorney, Agent, or Firm* — Wolf, Greenfield & Sacks, P.C.

(57) ABSTRACT

The present invention provides a method of detecting mutational signatures in a DNA sample. The invention relates to method of detecting signatures arising from rearrangements in the DNA in the sample and determining the contributions of known rearrangement signatures to said rearrangements. In particular embodiments, the contributions are determined by computing the cosine similarity between the rearrangement mutations in said catalogue and the rearrangement mutational signatures. The rearrangement signatures are classified based on whether they are clustered or not, whether they are tandem duplications, deletions, inversions or translocations and on the basis of their size.

17 Claims, 2 Drawing Sheets

(51) Int. Cl.
G16B 20/10 (2019.01)
G16B 40/00 (2019.01)
G16B 40/30 (2019.01)

(58) Field of Classification Search
USPC .......................................................... 702/19
See application file for complete search history.

(56) References Cited

U.S. PATENT DOCUMENTS

| | | |
|---|---|---|
| 2014/0363521 A1 | 12/2014 | Abkevich et al. |
| 2019/0115105 A1 | 4/2019 | Liu et al. |
| 2019/0119759 A1 | 4/2019 | Nik-Zainal et al. |
| 2019/0130997 A1 | 5/2019 | Nik-Zainal et al. |
| 2019/0139625 A1 | 5/2019 | Nik-Zainal et al. |
| 2020/0126635 A1 | 4/2020 | Nik-Zainal et al. |

FOREIGN PATENT DOCUMENTS

| | | |
|---|---|---|
| EP | 3452938 | 11/2017 |
| JP | 2015/506678 A | 3/2015 |
| WO | WO-02/06481 A1 | 1/2002 |
| WO | WO 2008/016374 A2 | 2/2008 |
| WO | WO-2013/096843 A1 | 6/2013 |
| WO | WO-2013/182645 A1 | 12/2013 |
| WO | WO-2013/190441 A2 | 12/2013 |
| WO | WO-2015/086473 A1 | 6/2015 |
| WO | WO-2017/191068 A1 | 11/2017 |
| WO | WO-2017/191073 A1 | 11/2017 |
| WO | WO-2017/191074 A1 | 11/2017 |
| WO | WO-2017/191076 A1 | 11/2017 |

OTHER PUBLICATIONS

Volleberg et al., "Genomic instability in breast and ovarian cancers: translation into clinical predictive biomarkers," Cell Mol Life Sci. 69(2):223-45 (2012).
Combined Search and Examination Report Under Sections 17 and 18(3) for British Application No. 1706944.4, dated Feb. 8, 2018 (8 pages).
Nik-Zainal et al., "Mutational processes molding the genomes of 21 breast cancers," Cell. 149(5):979-93 (2012).
Notice of Reasons for Rejection and English Translation for Japanese Patent Application No. 2019-508296, dated Apr. 13, 2021 (5 pages).
Office Action for Japanese Patent Application No. 2018-557362, dated Aug. 3, 2021.
Chopra et al., "Homologous recombination DNA repair deficiency and PARP inhibition activity in primary triple negative breast cancer," Nat Commun. 11(1):2662 (2020) (12 pages).
Davies et al., "HRDetect is a predictor of BRCA1 and BRCA2 deficiency based on mutational signatures," available in PMC Mar. 2, 2018 published in final edited form as: Nat Med. 23(4):517-525 (2017) (28 pages).
Degasperi et al., "A practical framework and online tool for mutational signature analyses show intertissue variation and driver dependencies," available in PMC Feb. 28, 2020, published in final edited form as: Nat Cancer. 1(2):249-263 (2020) (45 pages).
Stratton et al., "The cancer genome," Nature. (458)7239:719-24 (2009).
Nik-Zainal et al., "The Life History of 21 Breast Cancers," Cell. 149(5):994-1007 (2012).
Hicks et al., "Novel patterns of genome rearrangement and their association with survival in breast cancer," Genome research. 16(12):1465-79 (2006).
Bergamaschi et al., "Extracellular matrix signature identifies breast cancer subgroups with different clinical outcome," J Pathol. 214(3):357-67 (2008) (Abstract only) (2 pages).
Ching et al., "Integrated analysis of copy number and loss of heterozygosity in primary breast carcinomas using high-density SNP array," Int J Oncol. 39(3):621-33 (2011).

Fang et al., "Genomic differences between estrogen receptor (ER)-positive and ER-negative human breast carcinoma identified by single nucleotide polymorphism array comparative genome hybridization analysis," available in PMC Jul. 31, 2015 published in final edited form as: Cancer. 117(10):2024-34 (2011) (17 pages).
Curtis et al., "The genomic and transcriptomic architecture of 2,000 breast tumours reveals novel subgroups," available in PMC Dec. 21, 2012 published in final edited form as: Nature. 486(7403):346-52 (2012) (15 pages).
Pleasance et al., "A comprehensive catalogue of somatic mutations from a human cancer genome," available in PMC Jul. 28, 2011, published in final edited form as: Nature. 463(7278):191-6 (2010) (14 pages).
Pleasance et al., "A small-cell lung cancer genome with complex signatures of tobacco exposure," Nature. 463(7278):184-90 (2010) (9 pages).
Banerji et al., "Sequence analysis of mutations and translocations across breast cancer subtypes," available in PMC Aug. 29, 2014, published in final edited form as: Nature. 486(7403):405-9 (2012) (11 pages).
Ellis et al., "Whole-genome analysis informs breast cancer response to aromatase inhibition," available in PMC Dec. 21, 2012, published in final edited form as: Nature. 486(7403):353-60 (2012) (20 pages).
Shah et al., "The clonal and mutational evolution spectrum of primary triple-negative breast cancers," available in PMC Dec. 16, 2013, published in final edited form as: Nature. 486(7403):395-9 (2012) (13 pages).
Alexandrov et al., "Signatures of mutational processes in human cancer," available in PMC Feb. 22, 2014, published in final edited form as: Nature. 500(7463):415-21 (2013) (24 pages).
Helleday et al., "Mechanisms underlying mutational signatures in human cancers," Nat Rev Genet. 15(9):585-98 (2014) (24 pages).
Birkbak et al., "Telomeric allelic imbalance indicates defective DNA repair and sensitivity to DNA-damaging agents," available in PMC Oct. 23, 2013, published in final edited form as: Cancer Discov. 2(4):366-375 (2012) (19 pages).
Popova et al., "Ploidy and large-scale genomic instability consistently identify basal-like breast carcinomas with BRCA1/2 inactivation," Cancer Res. 72(21):5454-62 (2012).
Fischer et al., "EMu: probabilistic inference of mutational processes and their localization in the cancer genome," Genome Biol. 14(4): R39 (2013) (10 pages).
Sherry et al., "dbSNP: the NCBI database of genetic variation," Nucleic Acids Res. 29(1):308-11 (2001).
1000 Genomes Project Consortium et al., "An integrated map of genetic variation from 1,092 human genomes," available in PMC May 1, 2013, published in final edited form as: Nature. 491(7422):56-65 (2012) (24 pages).
Fu et al., "Analysis of 6,515 exomes reveals the recent origin of most human protein-coding variants," available in PMC Jul. 10, 2013, published in final edited form as: Nature (493)7431:216-20 (2013) (11 pages).
Garassino, "Personalised Cancer Medicine: An ESMO Guide for Patients," ESMO, 1-46 (2013) (51 pages).
Timms et al., "Association of BRCA1/2 defects with genomic scores predictive of DNA damage repair deficiency among breast cancer subtypes," Breast Cancer Res. 16(6):475 (2014) (23 pages).
Stratton, "Exploring the genomes of cancer cells: progress and promise," Science. 331(6024):1553-8 (2011) (7 pages).
Telli et al., "Homologous Recombination Deficiency (HRD) Score Predicts Response to Platinum-Containing Neoadjuvant Chemotherapy in Patients with Triple-Negative Breast Cancer," available in PMC Oct. 1, 2019, published in final edited form as: Clin Cancer Res. 22(15):3764-73 (Aug. 1, 2016) (21 pages).
Polak et al., "A mutational signature reveals alterations underlying deficient homologous recombination repair in breast cancer," available in PMC Jul. 23, 2020, published in final edited form as: Nat Genet. 49(10):1476-86 (Oct. 2017) (22 pages).
Iolascon et al., "Frequent clonal loss of heterozygosity (LOH) in the chromosomal region 1p32 occurs in childhood T cell acute lymphoblastic leukemia (T-ALL) carrying rearrangements of the TAL1 gene," Leukemia. 11(3):359-63 (1997).

(56) References Cited

OTHER PUBLICATIONS

Communication pursuant to Article 94(3) EPC for European Patent Application No. 17720779.2, dated Mar. 11, 2022 (6 pages).
Communication pursuant to Article 94(3) EPC for European Patent Application No. 17721610.8, dated Apr. 5, 2022 (8 pages).
Communication pursuant to Article 94(3) EPC for European Application No. 17720140.7, dated Feb. 18, 2022 (7 pages).
Final Rejection for Japanese Application No. 2018-557362, dated Jul. 5, 2022 (4 pages).
Alexandrov, Ludmil B., Thesis. Chapter 2 of "Signatures of Mutational Processes in Human Cancer," Doctor of Philosophy, Darwin College, University of Cambridge, 2014 (247 pages).
Notice of the Second Office Action and English Translation for Chinese Patent Application No. 2017800273405, dated Aug. 12, 2022 (15 pages).
Bao et al., "Review of current methods, applications, and data management for the bioinformatics analysis of whole exome sequencing," Cancer Inform. 13(Suppl 2):67-82 (Sep. 21, 2014).
Ayers et al., "SNP selection in genome-wide and candidate gene studies via penalized logistic regression," Genet Epidemiol. 34(8):879-91 (Dec. 2010).
Marquard et al., "Pan-cancer analysis of genomic scar signatures associated with homologous recombination deficiency suggests novel indications for existing cancer drugs," Biomark Res. 3:9 (May 1, 2015) (10 pages).
Final Office Action for U.S. Appl. No. 16/096,731 dated Dec. 7, 2022.
Piraino et al., Beyond the exome: the role of non-coding somatic mutations in cancer. Annals of oncology. Feb. 1, 2016;27(2):240-8.
Abkevich et al., "Patterns of genomic loss of heterozygosity predict homologous recombination repair defects in epithelial ovarian cancer," Br J Cancer. 107(10):1776-1782 (2012).
Abkevich et al., "Supplementary Material for: Patterns of Genomic Loss of Heterozygosity Predict Homologous Recombination Repair Defects in Epithelial Ovarian Cancer," Br J Cancer. (2012) (20 pages).
Alexandrov et al., "A mutational signature in gastric cancer suggests therapeutic strategies," Nat Commun. 6:8683 (2015) (7 pages).
Alexandrov et al., "Clock-like mutational processes in human somatic cells," Nat Genet. 47(12):1402-1407, doi: 10.1038/ng.3441 (2015) (9 pages).
Alexandrov et al., "Deciphering Signatures of Mutational Processes Operative in Human Cancer," Cell Rep. 3(1):246-59 (2013).
Alexandrov, Ludmil B., Thesis: "Signatures of Mutational Processes in Human Cancer," Doctor of Philosophy, Darwin College, University of Cambridge, 2014 (247 pages).

Chan et al., "Clusters of Multiple Mutations: Incidence and Molecular Mechanisms," available in PMC Jan. 12, 2016, published in final edited form as: Annu Rev Genet. 49:243-67 (2015) (32 pages).
International Preliminary Report on Patentability for International Application No. PCT/EP2017/060279, dated Nov. 6, 2018 (7 pages).
International Preliminary Report on Patentability for International Application No. PCT/EP2017/060289, dated Nov. 6, 2018 (9 pages).
International Preliminary Report on Patentability for International Application No. PCT/EP2017/060294, dated Nov. 6, 2018 (10 pages).
International Preliminary Report on Patentability for International Application No. PCT/EP2017/060298, dated Nov. 6, 2018 (8 pages).
International Search Report and Written Opinion for International Application No. PCT/EP2017/060279, dated Aug. 31, 2017 (10 pages).
International Search Report and Written Opinion for International Application No. PCT/EP2017/060289, dated Jul. 17, 2017 (12 pages).
International Search Report and Written Opinion for International Application No. PCT/EP2017/060294, dated Jul. 31, 2017 (15 pages).
International Search Report and Written Opinion for International Application No. PCT/EP2017/060298, dated Aug. 2, 2017 (12 pages).
Malhotra et al., "Breakpoint profiling of 64 cancer genomes reveals numerous complex rearrangements spawned by homology-independent mechanisms," Genome Research. 23(5): 762-776 (2013) (17 Pages).
Menghi et al., "The tandem duplicator phenotype as a distinct genomic configuration in cancer," Proc Natl Acad Sci USA. 113(17):E2373-E2382 (2016).
Nik-Zainal et al., "Landscape of somatic mutations in 560 breast cancer whole genome sequences," available in PMC Nov. 2, 2016, published in final edited form as: Nature. 534(7605):47-54 (2016) (40 pages).
Nik-Zainal, Serena, Thesis: "Exploring mutational signatures in twenty-one breast cancers," Doctor of Philosophy, University of Cambridge, 2012 (235 pages).
Pleasance et al., "A small-cell lung cancer genome with complex signatures of tobacco exposure," Nature. 463(7278): 184-190 (2009) (9 Pages).
Schulze et al., "Exome sequencing of hepatocellular carcinomas identifies new mutational signatures and potential therapeutic targets," available in PMC Nov. 1, 2015, published in final edited form as: Nature Genet. 47(5):505-11 (2015) (22 pages).

* cited by examiner

METHOD OF DETECTING A MUTATIONAL SIGNATURE IN A SAMPLE

Related Applications

This application is a national stage filing under 35 U.S.C. § 371 of international application number PCT/EP2017/060279, filed Apr. 28, 2017, which claims the benefit of Great Britain application number GB 1607628.3, filed May 1, 2016, each of which is herein incorporated by reference in its entirety.

FIELD OF INVENTION

The present invention relates to a method for detecting mutational signatures in a DNA sample. It is particularly concerned with a method for detecting rearrangement signatures in a DNA sample.

BACKGROUND TO THE INVENTION

Somatic mutations are present in all cells of the human body and occur throughout life. They are the consequence of multiple mutational processes, including the intrinsic slight infidelity of the DNA replication machinery, exogenous or endogenous mutagen exposures, enzymatic modification of DNA and defective DNA repair. Different mutational processes generate unique combinations of mutation types, termed "Mutational Signatures".

In the past few years, large-scale analyses have revealed many mutational signatures across the spectrum of human cancer types.

The mutational theory of cancer proposes that changes in DNA sequence, termed "driver" mutations, confer proliferative advantage upon a cell, leading to outgrowth of a neoplastic clone [1]. Some driver mutations are inherited in the germline, but most arise in somatic cells during the lifetime of the cancer patient, together with many "passenger" mutations not implicated in cancer development [1]. Multiple mutational processes, including endogenous and exogenous mutagen exposures, aberrant DNA editing, replication errors and defective DNA maintenance, are responsible for generating these mutations [1-3].

Over the past five decades, several waves of technology have advanced the characterisation of mutations in cancer genomes. Karyotype analysis revealed rearranged chromosomes and copy number alterations. Subsequently, loss of heterozygosity analysis, hybridisation of cancer-derived DNA to microarrays and other approaches provided higher resolution insights into copy number changes [4-8]. Recently, DNA sequencing has enabled systematic characterisation of the full repertoire of mutation types including base substitutions, small insertions/deletions, rearrangements and copy number changes [9-13], yielding substantial insights into the mutated cancer genes and mutational processes operative in human cancer.

Mutational processes generating somatic mutations imprint particular patterns of mutations on cancer genomes, termed signatures [2, 15, 16]. Applying a mathematical approach [15] to extract mutational signatures previously revealed five base substitution signatures in breast cancer; signatures 1, 2, 3, 8 and 13 [2,14].

Whilst base substitution signatures have been investigated and methods for their detection proposed, signatures of rearrangement mutational processes have not previously been formally investigated and in particular no methods proposed for the characterisation of rearrangement mutational signatures and identification of the presence of one or more rearrangement signatures in a DNA sample taken from a single patient.

A method of identifying the presence of rearrangement signatures in a DNA sample taken from a single patient would provide for considerable benefit as it may provide a potential route for diagnosis of possible cancer types in that patient or may provide identification of an underlying defect and therefore allow selection of patients for particular types of therapy.

STATEMENTS OF INVENTION

An exemplary embodiment of the present invention provides a method of detecting rearrangement signatures in a previously obtained DNA sample, the method including the steps of: cataloguing the somatic mutations in said sample to produce a rearrangement catalogue for that sample which classifies identified rearrangement mutations in the sample into a plurality of categories; determining the contributions of known rearrangement signatures to said rearrangement catalogue by computing the cosine similarity between the rearrangement mutations in said catalogue and the rearrangement mutational signatures.

A further exemplary embodiment of the present invention provides a computer program product containing non-transitory memory storing a computer program which, when run on a computer, performs the steps of: cataloguing the somatic mutations in said sample to produce a rearrangement catalogue for that sample which classifies identified rearrangement mutations in the sample into a plurality of categories; determining the contributions of known rearrangement signatures to said rearrangement catalogue by computing the cosine similarity between the rearrangement mutations in said catalogue and the rearrangement mutational signatures.

A further exemplary embodiment of the present invention provides a computer having a processor, wherein the processor is configured to: catalogue the somatic mutations in said sample to produce a rearrangement catalogue for that sample which classifies identified rearrangement mutations in the sample into a plurality of categories; determine the contributions of known rearrangement signatures to said rearrangement catalogue by computing the cosine similarity between the rearrangement mutations in said catalogue and the rearrangement mutational signatures.

BRIEF DESCRIPTION OF THE FIGURES & TABLE

Table 1 shows a quantitative definition of a number of rearrangement signatures.

DETAILED DESCRIPTION

A first aspect of the present invention provides a method of detecting rearrangement signatures in a previously obtained DNA sample, the method including the steps of: cataloguing the somatic mutations in said sample to produce a rearrangement catalogue for that sample which classifies identified rearrangement mutations in the sample into a plurality of categories; and determining the contributions of known rearrangement signatures to said rearrangement catalogue by computing the cosine similarity between the rearrangement mutations in said catalogue and the rearrangement mutational signatures.

Preferably the method includes the further step of, prior to said step of determining, filtering the mutations in said catalogue to remove either residual germline structural variations or known sequencing artefacts or both. Such filtering can be highly advantageous to remove rearrangements from the catalogue which are known to arise from mechanisms other than somatic mutation, and may therefore cloud or obscure the contributions of the rearrangement signatures, or lead to false positive results.

For example, the filtering may use a list of known germline rearrangement or copy number polymorphisms and remove somatic mutations resulting from those polymorphisms from the catalogue prior to determining the contributions of the rearrangement signatures.

As a further example, the filtering may use BAM files of unmatched normal human tissue sequenced by the same process as the DNA sample and discards any somatic mutation which is present in at least two well-mapping reads in at least two of said BAM files. This approach can remove artefacts resulting from the sequencing technology used to obtain the sample.

The classification of the rearrangement mutations may include identifying mutations as being clustered or non-clustered. This may be determined by a piecewise-constant fitting ("PCF") algorithm which is a method of segmentation of sequential data. In particular embodiments, rearrangements may be identified as being clustered if the average density of rearrangement breakpoints within a segment is a certain factor greater than the whole genome average density of rearrangements for an individual patient's sample. For example the factor may be at least 8 times, preferably at least 9 times and in particular embodiments is 10 times. The inter-rearrangement distance is the distance from a rearrangement breakpoint to the one immediately preceding it in the reference genome. For any given breakpoint, this measurement is already known.

The classification of the rearrangement mutations may include identifying rearrangements as one of: tandem duplications, deletions, inversions or translocations. Such classifications of rearrangement mutations are already known.

The classification of the rearrangement mutations may further include grouping mutations identified as tandem duplications, deletions or inversions by size. For example, the mutations may be grouped into a plurality of size groups by the number of bases in the rearrangement. Preferably the size groups are logarithmically based, for example 1-10 kb, 10-100 kb, 100 kb-1 Mb, 1 Mb-10 Mb and greater than 10 Mb. Translocations cannot be classified by size.

In particular embodiments, in each DNA sample the number of rearrangements $E_i$ associated with the ith mutational signature $\vec{S}_i$ is determined as proportional to the cosine similarity ($\vec{C}_i$) between the catalogue of this sample $\vec{M}$ and $\vec{S}_i$:

$$\vec{C}_i = \frac{\vec{S}_i \cdot \vec{M}}{\|\vec{S}_i\| \|\vec{M}\|}$$

wherein:

$$E_i = \frac{\vec{C}_i}{\sum_{i=1}^{q} \vec{C}_i} \sum_{j=1}^{36} \vec{M}^j$$

wherein $\vec{S}_i$ and $\vec{M}$ are equally-sized vectors with nonnegative components being, respectively, a known rearrangement signature and the mutational catalogue and q is the number of signatures in said plurality of known rearrangement signatures.

The method may further include the step of filtering the number of rearrangements determined to be assigned to each signature by reassigning one or more rearrangements from signatures that are less correlated with the catalogue to signatures that are more correlated with the catalogue. Such filtering can serve to reassign rearrangements from a signature which has only a few rearrangements associated with it (and so is probably not present) to a signature which has a greater number of rearrangement associated with it. This can have the effect of reducing "noise" in the assignment process.

In one embodiment, the step of filtering uses a greedy algorithm to iteratively find an alternative assignment of rearrangements to signatures that improves or does not change the cosine similarity between the catalogue $\vec{M}$ and the reconstructed catalogue $\vec{M}'=S\times\vec{E}_{ij}'$, wherein $\vec{E}_{ij}'$ is the version of the vector $\vec{E}$ obtained by moving the mutations from the signature i to signature j, wherein, in each iteration, the effects of all possible movements between signatures are estimated, and the filtering step terminates when all of these possible reassignments have a negative impact on the cosine similarity.

The subject may be a cancer patient or a suspected cancer patient. For example, the method may be used in the determination or identification of a rearrangement sequence to predict whether the subject has cancer or not or what type of cancer a patient has, or to select the subject for a particular form of treatment.

The method may further include the step of determining if the number or proportion of rearrangements in the rearrangement catalogue which are determined to be associated with one or more of said rearrangement signatures each or in combination exceeds a predetermined threshold and, if so, determining that said rearrangement signature is present in the sample.

The present inventors have determined that, by classifying rearrangement mutations by clustered/non-clustered, type and size (where appropriate), clear rearrangement signatures can be identified in a number of tumours. Accordingly, these classifications, in conjunction with the method of the present embodiment can provide an ability to identify the presence of particular rearrangement signatures and therefore determine a likelihood that a sample from a patient is indicative of the presence of a tumour and/or the form of cancer causing the tumour. As different forms of cancer are known to react different to particular treatments, the identification of the likely form of cancer present in a sample can guide the selection of the treatment for the subject.

The present inventors have also identified clear links between the rearrangement signatures and the underlying mechanisms contributing to a cancer. Accordingly, the presence (or absence) of a particular rearrangement signature (or collection of rearrangement signatures) can alternatively or additionally be used to determine the underlying mechanisms that are contributing to the tumour from which the sample is taken.

The method of the present aspect may include any combination of some, all or none of the above described preferred and optional features.

Further aspects of the present invention include computer programs for running on computer systems which carry out the method of the above aspect, including some, all or none of the preferred and optional features of that aspect.

A further aspect of the present invention provides a computer program product containing non-transitory memory storing a computer program which, when run on a computer, performs the steps of: cataloguing the somatic mutations in said sample to produce a rearrangement catalogue for that sample which classifies identified rearrangement mutations in the sample into a plurality of categories; determining the contributions of known rearrangement signatures to said rearrangement catalogue by computing the cosine similarity between the rearrangement mutations in said catalogue and the rearrangement mutational signatures.

A further aspect of the present invention provides a computer having a processor, wherein the processor is configured to: catalogue the somatic mutations in said sample to produce a rearrangement catalogue for that sample which classifies identified rearrangement mutations in the sample into a plurality of categories; determine the contributions of known rearrangement signatures to said rearrangement catalogue by computing the cosine similarity between the rearrangement mutations in said catalogue and the rearrangement mutational signatures.

The computer program and the processor of the above two aspects may also carry out some or all of the optional or preferred steps described above in relation to the first aspect.

These and other aspects of the invention are described in further detail below.

Identification of Rearrangement Signatures Linked to Cancer

The complete genomes of 560 breast cancers and non-neoplastic tissue from each individual (556 female and four male) were sequenced. 3,479,652 somatic base substitutions, 371,993 small indels and 77,695 rearrangements were detected, with substantial variation in the number of each between individual samples.

To enable investigation of signatures of rearrangement mutational processes, a rearrangement classification was adopted incorporating 32 subclasses.

In many cancer genomes, large numbers of rearrangements are regionally clustered, for example in zones of gene amplification. Therefore, the rearrangements were first classified into those that occurred as clusters or were dispersed, further sub-classified into deletions, inversions and tandem duplications, and then according to the size of the rearranged segment. The final category in both groups was interchromosomal translocations.

Figure 2:
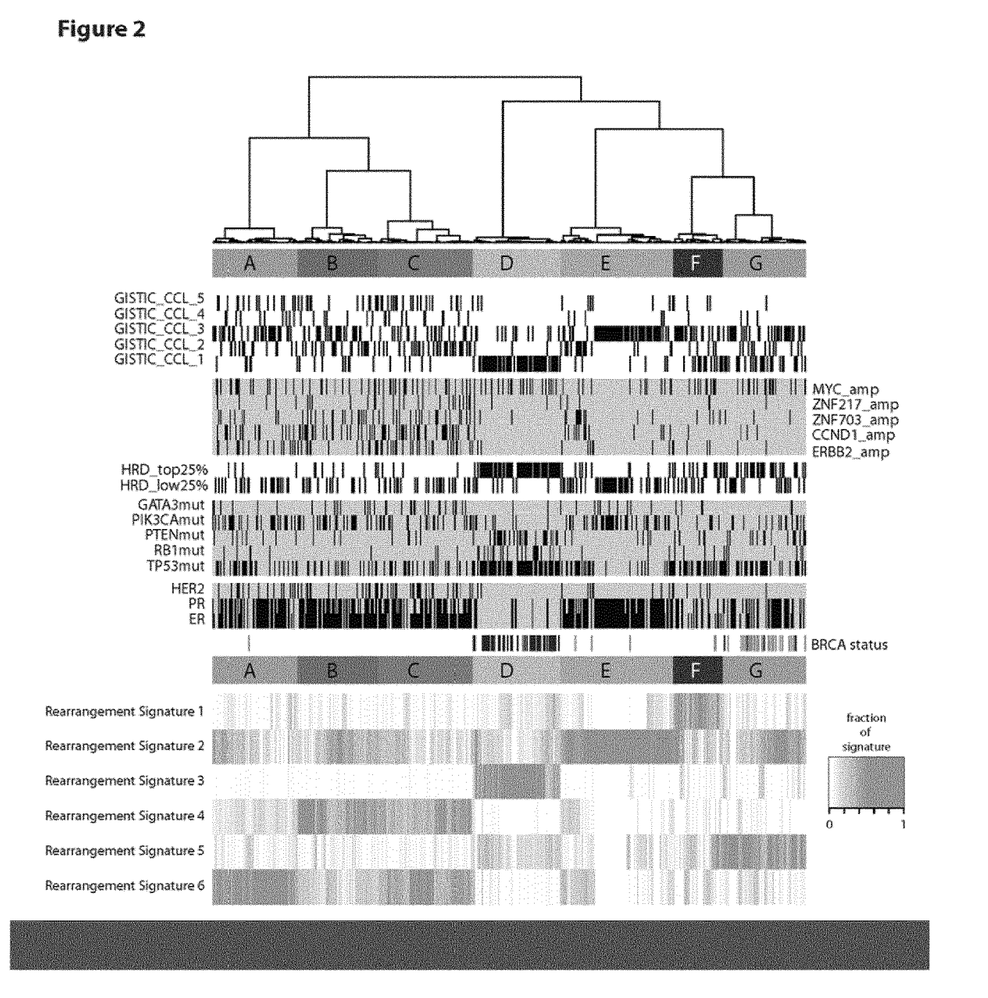
FIG. 2 is a diagram showing seven major subgroups exhibiting distinct associations with other genomic, histological or gene expression features, along with the six rearrangement signatures extracted from the data.

Application of the mathematical framework used for base substitution signatures [2, 14, 15] extracted six rearrangement signatures. Unsupervised hierarchical clustering on the basis of the proportion of rearrangements attributed to each signature in each breast cancer yielded seven major subgroups exhibiting distinct associations with other genomic, histological or gene expression features as shown in FIG. 2.

Rearrangement Signature 1 (9% of all rearrangements) and Rearrangement Signature 3 (18% rearrangements) were characterised predominantly by tandem duplications. Tandem duplications associated with Rearrangement Signature 1 were mostly >100 kb, and those with Rearrangement Signature 3<10 kb. More than 95% of Rearrangement Signature 3 tandem duplications were concentrated in 15% of cancers, many with several hundred rearrangements of this type. Almost all cancers (91%) with BRCA1 mutations or promoter hypermethylation were in this group, which was enriched for basal-like, triple negative cancers and copy number classification of a high Homologous Recombination Deficiency (HRD) index [17-19]. Thus, inactivation of BRCA1, but not BRCA2, may be responsible for the Rearrangement Signature 3 small tandem duplication mutator phenotype.

More than 35% of Rearrangement Signature 1 tandem duplications were found in just 8.5% of the breast cancers and some cases had hundreds of these. The cause of this large tandem duplication mutator phenotype is unknown. Cancers exhibiting it are frequently TP53-mutated, relatively late diagnosis, triple-negative breast cancers, showing enrichment for base substitution signature 3 and a high Homologous Recombination Deficiency (HRD) index but do not have BRCA1/2 mutations or BRCA1 promoter hypermethylation.

Rearrangement Signature 5 (accounting for 14% rearrangements) was characterised by deletions <100 kb. It was strongly associated with the presence of BRCA1 mutations or promoter hypermethylation (FIG. 2, Cluster D), BRCA2 mutations (FIG. 2, Cluster G) and with Rearrangement Signature 1 large tandem duplications (FIG. 2, Cluster F).

Rearrangement Signature 2 (accounting for 22% rearrangements) was characterised by non-clustered deletions (>100 kb), inversions and interchromosomal translocations, was present in most cancers but was particularly enriched in ER positive cancers with quiet copy number profiles (FIG. 2, Cluster E, GISTIC Cluster 3). Rearrangement Signature 4 (accounting for 18% of rearrangements) was characterised by clustered interchromosomal translocations while Rearrangement Signature 6 (19% of rearrangements) by clustered inversions and deletions (FIG. 2, Clusters A, B, C).

The methods according to embodiments of the invention set out below determine the presence or absence of a rearrangement signature in DNA samples obtained from a single patient. Preferably, these are whole genome samples and the presence or absence of mutational signatures may be determined by whole genome sequencing.

The DNA samples are preferably obtained from both tumour and normal tissues obtained from the patient, e.g. blood sample from the patient and breast tumour tissue obtained by a biopsy. Somatic mutations in the tumour sample are detected, standardly, by comparing its genomic sequences with the one of the normal tissue.

Method of Detection of Rearrangement Signatures in a Single Patient

In embodiments of the present invention, detection of a rearrangement signature in the DNA obtained from a single patient is performed. In these embodiments, this detection is performed by a computer-implemented method or tool that examines a list of somatic mutations generated through high-coverage or low-pass sequencing of nucleic acid material obtained from fresh-frozen derived DNA, circulating tumour DNA of formalin-fixed paraffin-embedded (FFPE) DNA representative of a suspected or known tumour from a patient. The steps of this method are illustrated schematically in FIG. 1.

The list of somatic mutations for these embodiments can be provided in variety of different formats (including, VCF, BEDPE, text etc.) but at the very minimum needs to contain the following information: genome assembly version, lower breakpoint chromosome, lower breakpoint coordinate, higher breakpoint chromosome, higher breakpoint coordinate and either rearrangement class (inversion, tandem duplication deletion, translocation) or strand information of lower and higher breakpoints to enable orientation of rearrangement breakpoints in order to correctly classify them.

Figure 1:
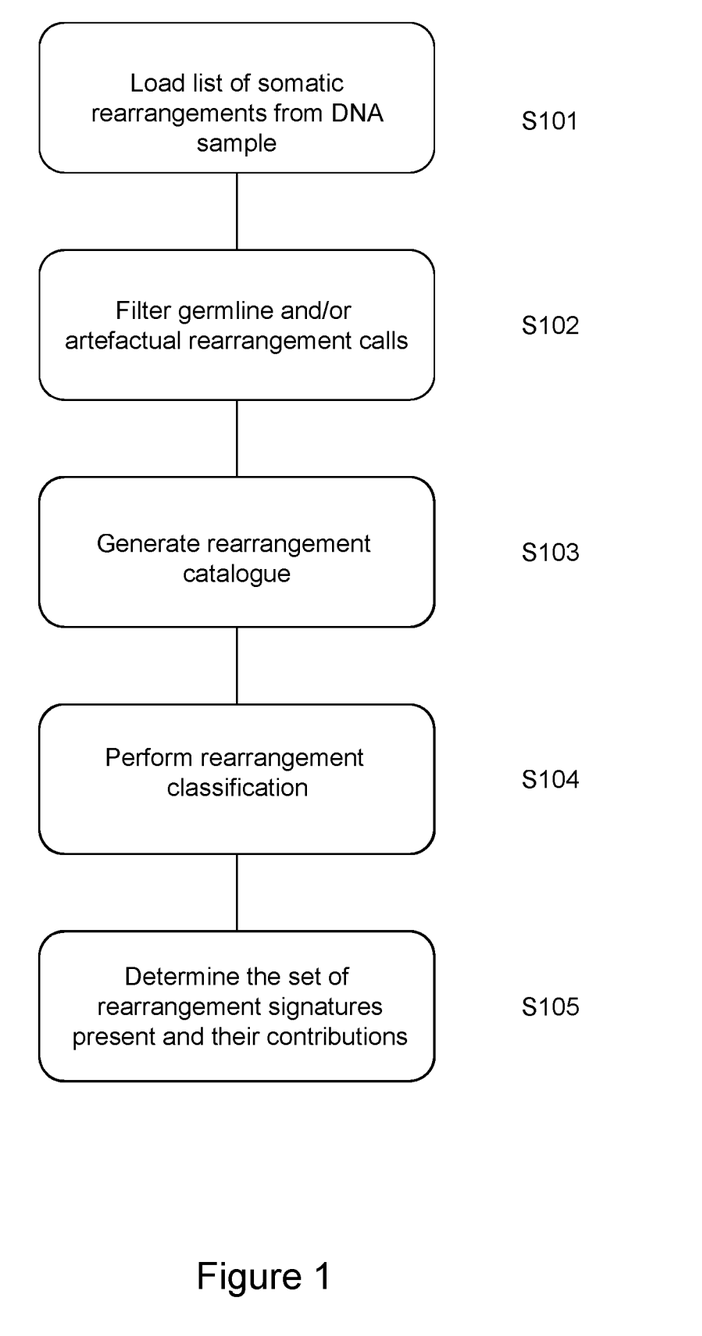
FIG. 1 is a flow diagram showing, in schematic form, a method of detecting a rearrangement signature in the DNA of a single patient according to an embodiment of the present invention.

In broad terms, after loading the list of somatic mutations from the DNA sample (S101) the tool firstly filters out any known germline and/or artifactual somatic mutations (S102), then generates the rearrangement catalogue of the sample, then classifies the rearrangements based on the classification described below (S103), then evaluates the contributions of known consensus rearrangement mutational signatures to this sample (S104) and finally determines the set of signatures of rearrangement processes, and their respective contributions, that are operative in the sample (S105).

By default, the patterns of the consensus rearrangement signatures are those shown in Table 1, but these patterns of mutational signatures could be also user provided and the method is not limited to known signatures and can be readily applied to new or modified signatures which are discovered in the future.

Filtering Initial Data

Prior to analysing the data, the input list of somatic rearrangements is extensively filtered to remove any residual germline mutations as well as technology specific sequencing artefacts.

Germline rearrangements or copy number polymorphisms are filtered out from the lists of reported somatic mutations using the complete list of germline mutations from dbSNP [21], 1000 genomes project [22], NHLBI GO Exome Sequencing Project [23] and 69 Complete Genomics panel (completegenomics.com/public-data/69-Genomes/).

Technology specific sequencing artefacts (related to library-making or sequencing chemistry) and mapping-related artefacts caused by errors or biases in the reference genome, are filtered out by using panels of BAM files of unmatched normal human tissues containing at least 100 normal whole-genomes. The remaining somatic mutations are used to construct the mutational catalogue of the examined sample.

Generating the Mutational Catalogue for a Sample

The list of remaining (i.e., post-filtered) somatic rearrangements is used to generate the rearrangement mutational catalogue of a sample.

(1) Clustered vs Non-Clustered

The first classification applied to the mutations is whether they are clustered (closely-grouped) or not.

To distinguish collections of rearrangements that are clustered or close together in a patient's cancer genome from other rearrangements that are distributed or dispersed throughout the genome, the data is parsed through a PCF-based algorithm. The PCF (Piecewise-Constant-Fitting) algorithm is a method of segmentation of sequential data.

Before applying PCF, a number of steps are performed on the rearrangement data.

Unlike substitutions or indels that have a single genomic coordinate to signify their position, rearrangements have two coordinates or "breakpoints" that identify two distant genomic loci that have been brought together by a large structural mutation event.

First, both breakpoints of each rearrangement are treated independently. The breakpoints are then sorted according to reference genomic coordinate in each sample. The intermutation distance (IMD), defined as the number of base pairs from one rearrangement breakpoint to the one immediately preceding it in the reference genome, is calculated for each breakpoint. The calculated IMD is then fed to the PCF algorithm.

To identify regions of "clustered" rearrangements from "non-clustered" rearrangements, a set of rearrangements was required to have an average density of rearrangement breakpoints that was at least 10 times greater than the whole genome average density of rearrangements for an individual patient's sample. Additionally, a gamma parameter (a measure of smoothness of segmentation) was stipulated, $\gamma=25$, and required that a minimum of 10 breakpoints were present in each region, before it could be classified as a cluster of rearrangements. Biologically, the respective partner breakpoint of any rearrangement involved in a clustered region is likely to have arisen at the same mechanistic instant and so can be considered as being involved in the cluster even if located at a distant genomic site according to the reference genome.

Thus rearrangements are first classified as "clustered" or "non-clustered.

(2) Type and Size

In both clustered and non-clustered categories, rearrangements are then classified based on the information provided into the main classes of rearrangements:

tandem duplications
deletions
inversions
translocations

Tandem duplications, deletions and inversions can then be categorised into the following 5 size groups where the size of a rearrangement is obtained through subtracting the lower breakpoint coordinate from the higher one.

1-10 kb
10-100 kb
100 kb-1 Mb
1 Mb-10 Mb
>10 Mb

Translocations are the exception and cannot be classified by size.

In all, there will be 16 subgroups of clustered and 16 subgroups of non-clustered rearrangements and thus 32 categories altogether. These are listed in Table 1.

The outcome of this classification can then be fed into a latent variable analysis such as NNMF, to obtain a non-negative vector of 32 elements describing each rearrangement signature.

Evaluating the Numbers of Somatic Mutations Attributed to Re-Arrangement Signatures in the Mutational Catalogue of the Examined Sample Calculating the contributions of all mutational signatures is performed by estimating the number of mutations associated to the consensus patterns of the signatures of all operative mutational processes in the sample. Below a method of estimating this using non-negative matrix factorisation (NNMF) is set out, although alternative methods such as EMU or a hierarchical Dirichlet process (HDP) may equally be used.

More specifically, all consensus rearrangement signatures are examined as a set P containing s vectors $$P = \left\{ \begin{bmatrix} p_1^1 \\ \vdots \\ p_1^{32} \end{bmatrix}, \begin{bmatrix} p_2^1 \\ \vdots \\ p_2^{32} \end{bmatrix} \cdots \begin{bmatrix} p_{s-1}^1 \\ \vdots \\ p_{s-1}^{32} \end{bmatrix}, \begin{bmatrix} p_s^1 \\ \vdots \\ p_s^{32} \end{bmatrix} \right\},$$

where each of the vectors is a discrete probability density function reflecting a consensus rearrangement signature. For the currently known rearrangement signatures, these vectors are set out in the respective columns of Table 1. Here, s refers to the number of known consensus rearrangement signatures (currently 6) and the 32 nonnegative components of each vector correspond to the different categories of rearrangements (i.e., clustered/non-clustered, type & size) of these consensus rearrangement signatures.

The contributions of all consensus rearrangement signatures are estimated independently for the mutational catalogue of the examined sample. The estimation algorithm consists of computing the cosine similarity between each signature and examined sample. For a set of vectors $S_1 \ldots q$, $q \leq s$, the cosine similarity $\vec{C}_i$ is given by:

$$\vec{C}_i = \frac{\vec{S}_i \cdot \vec{M}}{\|\vec{S}_i\| \|\vec{M}\|}$$

The number of rearrangements $E_i$ associated with the ith mutational signature $\vec{S}_i$ is proportional to the cosine similarity ($\vec{C}_i$):

$$E_i = \frac{\vec{C}_i}{\sum_{i=1}^{q} \vec{C}_i} \sum_{j=1}^{36} \vec{M}^j$$

wherein $\vec{S}_i$ and $\vec{M}$ are equally-sized vectors with nonnegative components being, respectively, a known rearrangement signature and the mutational catalogue and q is the number of signatures in said plurality of known rearrangement signatures.

In the above equation, $\vec{S}_i$ and $\vec{M}$ represent vectors with 32 nonnegative components (corresponding to the clustered/non-clustered characteristic and the type and size of the rearrangements) reflecting, respectively, a consensus mutational signature and the mutational catalogue of the examined sample. Hence, $\vec{S}_i \in \mathfrak{R}_+^{32}$ while $\vec{M} \in N_0^{32}$. Further, both vectors have known numerical values either from the consensus mutational signatures (i.e., $\vec{S}_i$) or from generating the original mutational catalogue of the sample (i.e., $\vec{M}$). In contrast, $E_i$ corresponds to an unknown scalar reflecting the number of rearrangements contributed by signature $\vec{S}_i$ in the mutational catalogue $\vec{M}$.

The above equation is universally constrained in regards to the parameter $E_i$. More specifically, the number of somatic rearrangements contributed by a rearrangement signature in a sample must be nonnegative and it must not exceed the total number of somatic mutations in that sample. Furthermore, the mutations contributed by all signatures in a sample must equal the total number of somatic mutations of that sample. These constraints can be mathematically expressed as $$0 \leq E_i \leq \|\vec{S}_i\|_1, \, i = 1..q, \text{ and } \sum_{i=1}^{q} E_i = \|\vec{S}_i\|_1.$$

When no prior biological knowledge is available the whole set Q of signatures is used in the determination of $E_i$, and a filter step is used to move the mutations from the least correlated signatures the ones that best explain the considered sample (signature highly correlated). Given the catalogue $\vec{M}$ and given all $\|Q^Q\|$ possible movements between two signatures i and j ($i \neq j$ and $i,j=1, \ldots, Q$), the filtering step uses a greedy algorithm to iteratively choose the movement that improves or does not change the cosine similarity between the catalogue $\vec{M}$ and the reconstructed catalogue $\vec{M}'=S \times \vec{E}_{ij}'$. ($\vec{E}_{ij}'$ is the version of the vector $\vec{E}$ obtained by moving the mutations from the signature i to signature j). The filtering step terminates when all the movement between signatures have a negative impact on the cosine similarity.

The filtering step can thus reduce the "noise" in the DNA sample which may initially result in the attribution of a small number of rearrangements to a signature which is not in fact present. The filtering allows such rearrangement to be reassigned to a signature which is more prevalent.

It is then possible to determine whether the sample exhibits one or more of the rearrangement signatures from the known rearrangement signatures from the number of rearrangements which are present in the sample and which are associated with a particular signature. Different thresholds for this determination may be set depending on the context and the desired certainty of the outcome. Generally the threshold will combine the total number of rearrangements detected in the sample (to ensure that the analysis is representative) along with a proportion of the rearrangements which are associated with a particular signature as determined by the above method.

For example, for data obtained from genomes sequenced to 30-40 fold depth, the requirements for detection may be that there are at least 20, preferably at least 40, more preferably at least 50 rearrangements and a signature is deemed to be present if a proportion of at least 10%, preferably at least 20%, more preferably at least 30% of the rearrangements are associated with it. As indicated below, the proportional thresholds may be adjusted depending on the number of other signatures which make up a significant portion of the rearrangements found in the sample (e.g., if 4 signatures are present each with 25% of the rearrangements, then it may be determined that all 4 are present, rather than no signatures at all are present, even if the general requirement for detection is set higher than 25%).

The rearrangement signatures are generally "additive" with respect to each other (i.e. a tumour may be affected by the underlying mutational processes associated with more than one signature and, if this is the case, a sample from that tumour will generally display a higher overall number of rearrangements (being the sum of the separate rearrangements associated with each of the underlying processes), but with the proportion of rearrangements spread over the signatures which are present). As a result, in determining the presence or absence of a particular signature, attention may be paid to the absolute number of rearrangements associated with a particular signature in the sample (as calculated by the method above). Such alternative requirements for detection can better account for the situation where multiple signatures are present. Under this approach, a signature may be determined to be present if at least 10 and preferably at least 20 rearrangements are associated with it.

The systems and methods of the above embodiments may be implemented in a computer system (in particular in computer hardware or in computer software) in addition to the structural components and user interactions described.

The term "computer system" includes the hardware, software and data storage devices for embodying a system or carrying out a method according to the above described embodiments. For example, a computer system may comprise a central processing unit (CPU), input means, output means and data storage. Preferably the computer system has a monitor to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

REFERENCES

1 Stratton, M. R., Campbell, P. J. & Futreal, P. A. The cancer genome. Nature 458, 719-724, doi:10.1038/nature07943 (2009).

2 Nik-Zainal, S. et al. Mutational processes molding the genomes of 21 breast cancers. Cell 149, 979-993, doi:10.1016/j.cell.2012.04.024 (2012).

3 Nik-Zainal, S. et al. The life history of 21 breast cancers. Cell 149, 994-1007, doi:10.1016/j.cell.2012.04.023 (2012).

4 Hicks, J. et al. Novel patterns of genome rearrangement and their association with survival in breast cancer. Genome research 16, 1465-1479, doi:10.1101/gr.5460106 (2006).

5 Bergamaschi, A. et al. Extracellular matrix signature identifies breast cancer subgroups with different clinical outcome. The Journal of pathology 214, 357-367, doi:10.1002/path.2278 (2008).

6 Ching, H. C., Naidu, R., Seong, M. K., Har, Y. C. & Taib, N. A. Integrated analysis of copy number and loss of heterozygosity in primary breast carcinomas using high-density SNP array. International journal of oncology 39, 621-633, doi:10.3892/ijo.2011.1081 (2011).

7 Fang, M. et al. Genomic differences between estrogen receptor (ER)-positive and ER-negative human breast carcinoma identified by single nucleotide polymorphism array comparative genome hybridization analysis. Cancer 117, 2024-2034, doi:10.1002/cncr.25770 (2011).

8 Curtis, C. et al. The genomic and transcriptomic architecture of 2,000 breast tumours reveals novel subgroups. Nature 486, 346-352, doi:10.1038/nature10983 (2012).

9 Pleasance, E. D. et al. A comprehensive catalogue of somatic mutations from a human cancer genome. Nature 463, 191-196, doi:10.1038/nature08658 (2010).

10 Pleasance, E. D. et al. A small-cell lung cancer genome with complex signatures of tobacco exposure. Nature 463, 184-190, doi:10.1038/nature08629 (2010).

11 Banerji, S. et al. Sequence analysis of mutations and translocations across breast cancer subtypes. Nature 486, 405-409, doi:10.1038/nature11154 (2012).

12 Ellis, M. J. et al. Whole-genome analysis informs breast cancer response to aromatase inhibition. Nature 486, 353-360, doi:10.1038/nature11143 (2012).

13 Shah, S. P. et al. The clonal and mutational evolution spectrum of primary triple-negative breast cancers. Nature 486, 395-399, doi:10.1038/nature10933 (2012).

14 Alexandrov, L. B. et al. Signatures of mutational processes in human cancer. Nature 500, 415-421, doi:10.1038/nature12477 (2013).

15 Alexandrov, L. B., Nik-Zainal, S., Wedge, D. C., Campbell, P. J. & Stratton, M. R. Deciphering signatures of mutational processes operative in human cancer. Cell reports 3, 246-259, doi:10.1016/j.celrep.2012.12.008 (2013).

16 Helleday, T., Eshtad, S. & Nik-Zainal, S. Mechanisms underlying mutational signatures in human cancers. Nature reviews. Genetics 15, 585-598, doi:10.1038/nrg3729 (2014).

17 Birkbak, N. J. et al. Telomeric allelic imbalance indicates defective DNA repair and sensitivity to DNA-damaging agents. Cancer discovery 2, 366-375, doi:10.1158/2159-8290.CD-11-0206 (2012).

18 Abkevich, V. et al. Patterns of genomic loss of heterozygosity predict homologous recombination repair defects in epithelial ovarian cancer. British journal of cancer 107, 1776-1782, doi:10.1038/bjc.2012.451 (2012).

19 Popova, T. et al. Ploidy and large-scale genomic instability consistently identify basal-like breast carcinomas with BRCA1/2 inactivation. Cancer research 72, 5454-5462, doi:10.1158/0008-5472.CAN-12-1470 (2012).

20 Fischer A, Illingworth C J, Campbell P J, Mustonen V.; EMu: probabilistic inference of mutational processes and their localization in the cancer genome Genome Biol. 2013 Apr. 29; 14(4):R39. doi: 10.1186/gb-2013-14-4-r39.

21 Sherry, S. T. et al. dbSNP: the NCBI database of genetic variation. Nucleic acids research 29, 308-311 (2001).

22 Abecasis, G. R. et al. An integrated map of genetic variation from 1,092 human genomes. Nature 491, 56-65, doi:10.1038/nature11632 (2012).

23 Fu, W. et al. Analysis of 6,515 exomes reveals the recent origin of most human protein-coding variants. Nature 493, 216-220, doi:10.1038/nature11690 (2013).

All of the above references are hereby incorporated by reference.

TABLE 1

| Type | Class | Size | Probability | | | | | |
| --- | --- | --- | --- | --- | --- | --- | --- | --- |
| | | | Signature 1 | Signature 2 | Signature 3 | Signature 4 | Signature 5 | Signature 6 |
| clustered | deletion | 1-10 kb | 0% | 0% | 0% | 1% | 0% | 1% |
| clustered | deletion | 10-100 kb | 0% | 0% | 0% | 1% | 0% | 1% |
| clustered | deletion | 100 kb-1 Mb | 0% | 0% | 0% | 2% | 0% | 3% |
| clustered | deletion | 1 Mb-10 Mb | 0% | 0% | 0% | 3% | 0% | 7% |

TABLE 1-continued

| Type | Class | Size | Probability | | | | | |
| --- | --- | --- | --- | --- | --- | --- | --- | --- |
| | | | Signature 1 | Signature 2 | Signature 3 | Signature 4 | Signature 5 | Signature 6 |
| clustered | deletion | >10 Mb | 0% | 0% | 0% | 1% | 0% | 7% |
| clustered | tandem duplication | 1-10 kb | 0% | 0% | 0% | 0% | 0% | 0% |
| clustered | tandem duplication | 10-100 kb | 0% | 0% | 0% | 1% | 0% | 1% |
| clustered | tandem duplication | 100 kb-1 Mb | 1% | 0% | 0% | 1% | 0% | 3% |
| clustered | tandem duplication | 1 Mb-10 Mb | 0% | 0% | 0% | 3% | 0% | 7% |
| clustered | tandem duplication | >10 Mb | 0% | 0% | 0% | 1% | 0% | 7% |
| clustered | inversion | 1-10 kb | 0% | 0% | 0% | 3% | 0% | 2% |
| clustered | inversion | 10-100 kb | 0% | 0% | 0% | 2% | 0% | 2% |
| clustered | inversion | 100 kb-1 Mb | 0% | 0% | 0% | 3% | 0% | 5% |
| clustered | inversion | 1 Mb-10 Mb | 0% | 0% | 0% | 6% | 0% | 15% |
| clustered | inversion | >10 Mb | 0% | 0% | 0% | 2% | 0% | 14% |
| clustered | translocation | | 0% | 0% | 0% | 56% | 0% | 0% |
| non-clustered | deletion | 1-10 kb | 0% | 2% | 2% | 0% | 32% | 3% |
| non-clustered | deletion | 10-100 kb | 1% | 1% | 0% | 0% | 22% | 2% |
| non-clustered | deletion | 100 kb-1 Mb | 4% | 5% | 0% | 0% | 5% | 2% |
| non-clustered | deletion | 1 Mb-10 Mb | 1% | 6% | 0% | 1% | 1% | 2% |
| non-clustered | deletion | >10 Mb | 0% | 6% | 1% | 0% | 1% | 2% |
| non-clustered | tandem duplication | 1-10 kb | 0% | 0% | 53% | 0% | 1% | 0% |
| non-clustered | tandem duplication | 10-100 kb | 16% | 0% | 22% | 0% | 12% | 0% |
| non-clustered | tandem duplication | 100 kb-1 Mb | 54% | 0% | 1% | 0% | 1% | 0% |
| non-clustered | tandem duplication | 1 Mb-10 Mb | 17% | 2% | 0% | 1% | 0% | 1% |
| non-clustered | tandem duplication | >10 Mb | 0% | 5% | 1% | 0% | 1% | 1% |
| non-clustered | inversion | 1-10 kb | 1% | 5% | 1% | 1% | 5% | 1% |
| non-clustered | inversion | 10-100 kb | 2% | 2% | 0% | 0% | 3% | 1% |
| non-clustered | inversion | 100 kb-1 Mb | 2% | 4% | 0% | 0% | 0% | 1% |
| non-clustered | inversion | 1 Mb-10 Mb | 0% | 10% | 0% | 1% | 0% | 4% |
| non-clustered | inversion | >10 Mb | 1% | 12% | 1% | 0% | 2% | 3% |
| non-clustered | translocation | | 1% | 39% | 16% | 7% | 13% | 1% |

The invention claimed is:

1. A method of detecting rearrangement signatures in a previously obtained DNA sample from a patient, the method comprising:
   obtaining whole genome DNA sequence data from said DNA sample by sequencing nucleic acid material obtained from the DNA sample, wherein the DNA sample comprises fresh-frozen derived DNA, circulating tumor DNA, or formalin-fixed paraffin-embedded (FFPE) DNA representative of a suspected or known tumor from the patient;
   obtaining, by a processor, a file of somatic mutations in the DNA sample, the somatic mutations obtained from the whole genome DNA sequence data;
   filtering, by the processor and using data obtained from one or more databases, the somatic mutations in the file to remove one or more germline rearrangements and copy number polymorphisms;
   filtering, by the processor and using data in alignment mapping files, the somatic mutations in the file to remove known sequencing artifacts;
   cataloguing, by the processor, the somatic mutations in the file to produce a rearrangement catalogue for the DNA sample which classifies rearrangement mutations identified in the whole genome DNA sequence data into a plurality of categories, the cataloguing comprising:
      identifying mutations as one of: tandem duplications, deletions, inversions or translocations and grouping mutations identified as tandem duplications, deletions or inversions by size, and
      identifying mutations as being clustered or non-clustered;
   determining, by said processor, the contributions of known rearrangement signatures to said rearrangement catalogue using a measure of similarity between the rearrangement mutations in said rearrangement catalogue and the known rearrangement signatures, wherein each of the known rearrangement signatures comprises proportions of rearrangements in the plurality of categories and wherein said known rearrangement signatures are indicative of the presence of mutational processes contributing to cancer; and
   determining, by the processor, if the number or proportion of rearrangements in the rearrangement catalogue which are determined to be associated with a particular one of the known rearrangement signatures exceeds a predetermined threshold and, if so, determining that the particular one rearrangement signature is present in the DNA sample.

2. The method according to claim 1 wherein determining, by said processor, the contributions of known rearrangement signatures to said rearrangement catalogue using the measure of similarity between the rearrangement mutations in said rearrangement catalogue and the known rearrangement signatures comprises:

determining a cosine similarity between the rearrangement mutations in said rearrangement catalogue and the known rearrangement signatures.

3. The method according to claim 1, wherein filtering, by the processor and using the data obtained from one or more databases, the somatic mutations in the file to remove one or more germline rearrangements and copy number polymorphisms comprises:
   filtering the somatic mutations using reported somatic mutations obtained from the one or more databases.

4. The method according to claim 1, wherein filtering, by the processor and using data in alignment mapping files, the somatic mutations in the file to remove known sequencing artifacts comprises:
   filtering the somatic mutations using compressed binary versions of sequence alignment map (BAMS) files of unmatched normal human tissue, the BAM files sequenced by the same process as the DNA sample, the filtering comprising discarding any somatic mutation which is present in at least two well-mapping reads in at least two of said BAM files.

5. The method according to claim 1, wherein identifying mutations as being clustered or non-clustered comprises identifying mutations as clustered if the mutations have an average density of rearrangement breakpoints that is at least 10 times greater the whole genome average density of rearrangements for an individual patient's sample.

6. The method according to claim 1, further comprising:
   determining the number of rearrangements $E_i$ in the rearrangement catalogue associated with the ith known mutational signature $\vec{S}_i$ which is proportional to a cosine similarity ($\vec{C}_i$) between a catalogue of the DNA sample $\vec{M}$ and $\vec{S}_i$:

$$\vec{C}_i = \frac{\vec{S}_i \cdot \vec{M}}{\|\vec{S}_i\| \|\vec{M}\|}$$

wherein:

$$E_i = \frac{\vec{C}_i}{\sum_{k=1}^{q} \vec{C}_i} \sum_{j=1}^{36} \vec{M}^j$$

wherein $\vec{S}_i$ and $\vec{M}$ are equally-sized vectors with non-negative components being, respectively, a known rearrangement signature and the rearrangement catalogue, n is the number of categories in said rearrangement catalogue, and q is the number of signatures in said known rearrangement signatures, and wherein $E_i$, are further constrained by the requirements that $$0 \leq E_i \leq \|\vec{S}_i\|_1, i = 1..q, \text{ and } \sum_{k=1}^{q} E_i = \|\vec{S}_i\|_1.$$

7. The method according to claim 6, wherein determining the number of rearrangements further comprises:
   filtering the number of rearrangements determined to be assigned to each signature by reassigning one or more rearrangements from signatures that are less correlated with the rearrangement catalogue to signatures that are more correlated with the rearrangement catalogue.

8. The method according to claim 7, further comprising:
   using a greedy algorithm to iteratively find an alternative assignment of rearrangements to signatures that improves or does not change the cosine similarity between the catalogue $\vec{M}$ and a reconstructed catalogue $\vec{M}' = S \times \vec{E}_{ij}'$, wherein $\vec{E}_{ij}'$ is the version of the vector $\vec{E}$ obtained by moving the mutations from the signature i to signature j.

9. The method according to claim 1, wherein identifying mutations as being clustered or non-clustered comprises:
   sorting breakpoints of rearrangements in the rearrangement catalogue according to their reference genomic coordinates to obtain a sorted order of breakpoints;
   determining intermutation distances between neighboring breakpoints in the sorted order of breakpoints; and
   applying a piecewise-constant-fitting (PCF) algorithm to the intermutation distances.

10. The method of claim 1,
    wherein the known rearrangement signatures include a rearrangement signature characterized by the presence of non-clustered tandem duplications less than 10kb in length, and
    wherein determining by said processor, the contributions of the known rearrangement signatures to said rearrangement catalogue comprises: determining, by said processor, the contribution of the rearrangement signature characterized by the presence of non-clustered tandem duplications less than 10kb in length to said rearrangement catalogue using the measure of similarity.

11. The method of claim 10, further comprising:
    determining that the rearrangement signature characterized by the presence of non-clustered tandem duplications less than 10kb in length is present in the DNA sample by determining if the number or proportion of rearrangements in the rearrangement catalogue which are determined to be associated with the rearrangement signature characterized by the presence of non-clustered tandem duplications less than 10kb in length exceeds a predetermined threshold; and
    selecting the patient for treatment with a particular cancer therapy for patients whose cancer exhibit homologous recombination deficiency (HRD) when it is determined that the rearrangement signature characterized by the presence of non-clustered tandem duplications less than 10kb in length is present in the DNA sample.

12. The method of claim 11, further comprising:
    administering the particular cancer therapy to the patient.

13. A computer program product containing non-transitory memory storing a computer program which, when run on a computer, performs a method comprising:
    obtaining whole genome DNA sequence data that was previously obtained by sequencing a DNA sample, the DNA sample comprising fresh-frozen derived DNA, circulating tumor DNA, or formalin-fixed paraffin-embedded (FFPE) DNA representative of a suspected or known tumor from a patient;
    obtaining a file of somatic mutations in the DNA sample, the somatic mutations obtained from the whole genome DNA sequence data;
    filtering, using data obtained from one or more databases, the somatic mutations in the file to remove one or more germline rearrangements and copy number polymorphisms;

filtering, using data in alignment mapping files, the somatic mutations in the file to remove known sequencing artifacts;

cataloguing the somatic mutations in the file to produce a rearrangement catalogue for the DNA sample which classifies rearrangement mutations identified in the sequence data into a plurality of categories, the cataloguing comprising:

identifying mutations as one of: tandem duplications, deletions, inversions or translocations and grouping mutations identified as tandem duplications, deletions or inversions by size, and identifying mutations as being clustered or non-clustered;

determining the contributions of known rearrangement signatures to said rearrangement catalogue using a measure of similarity between the rearrangement mutations in said rearrangement catalogue and the known rearrangement signatures, wherein each of the known rearrangement signatures comprises proportions of rearrangements in the plurality of categories and wherein said known rearrangement signatures are indicative of the presence of mutational processes contributing to cancer; and determining if the number or proportion of rearrangements in the rearrangement catalogue which are determined to be associated with a particular one of the known rearrangement signatures exceeds a predetermined threshold and, if so, determining that the particular one rearrangement signature is present in the DNA sample.

14. A computer system comprising:

a processor; and a non-transitory computer readable medium storing a computer program which when run by the processor, causes the processor to:

obtain sequence data previously obtained by sequencing a DNA sample of a patient, the DNA sample comprising fresh-frozen derived DNA, circulating tumor DNA, or formalin-fixed paraffin-embedded (FFPE) DNA representative of a suspected or known tumor from the patient;

obtain a file of somatic mutations in the DNA sample, the somatic mutations obtained from the sequence data;

filter, using data obtained from one or more databases, the somatic mutations in the file to remove one or more germline rearrangements and copy number polymorphisms;

filter, using data in alignment mapping files, the somatic mutations in the file to remove known sequencing artifacts;

catalogue the somatic mutations in the file to produce a rearrangement catalogue for the DNA sample which classifies rearrangement mutations identified in the sequence data into a plurality of categories, the cataloguing comprising:

identifying mutations as one of: tandem duplications, deletions, inversions or translocations and grouping mutations identified as tandem duplications, deletions or inversions by size, and identifying mutations as being clustered or non-clustered;

determine the contributions of known rearrangement signatures to said rearrangement catalogue using a measure of similarity between the rearrangement mutations in said rearrangement catalogue and the known rearrangement signatures, wherein each of the known rearrangement signatures comprises proportions of rearrangements in the plurality of categories and wherein said known rearrangement signatures are indicative of the presence of mutational processes contributing to cancer; and determine if the number or proportion of rearrangements in the rearrangement catalogue which are determined to be associated with a particular one of the known rearrangement signatures exceeds a predetermined threshold and, if so, determining that the particular one rearrangement signature is present in the DNA sample.

15. A method of selecting a subject for a particular treatment for cancer and treating the subject using the particular treatment for cancer, the method comprising:

detecting rearrangement signatures in a previously obtained DNA sample from said subject wherein each of the rearrangement signatures comprises proportions of rearrangements in each of a plurality of categories, wherein the rearrangement signatures include a rearrangement signature characterized by the presence of non-clustered tandem duplications less than 10kb in length, and wherein detecting the rearrangement signatures comprises:

cataloguing, by a processor, somatic mutations in sample using whole genome DNA sequence data obtained from the DNA sample to produce a rearrangement catalogue for the DNA sample which classifies rearrangement mutations identified in the whole genome DNA sequence data into the plurality of categories; and determining, by said processor, the contributions of the rearrangement signatures, including the rearrangement signature characterized by the presence of non-clustered tandem duplications less than 10kb in length, to said rearrangement catalogue by computing a measure of similarity between the rearrangement mutations in said rearrangement catalogue and the rearrangement signatures, the computing comprising computing the measure of similarity between the rearrangement mutations in said rearrangement catalogue and the rearrangement signature characterized by the presence of non-clustered tandem duplications less than 10kb in length;

determining that the rearrangement signature characterized by the presence of non-clustered tandem duplications less than 10kb in length is present in the DNA sample by determining if the number or proportion of rearrangements in the rearrangement catalogue which are determined to be associated with the rearrangement signature characterized by the presence of non-clustered tandem duplications less than 10kb in length exceeds a predetermined threshold;

selecting the subject for treatment with a particular cancer therapy for subjects whose cancer exhibit homologous recombination deficiency (HRD) when it is determined that the rearrangement signature characterized by the presence of non-clustered tandem duplications less than 10kb in length is present in the DNA sample; and administering the particular cancer therapy to the subject, and wherein the processor cataloguing the somatic mutations in said DNA sample to produce said rearrangement catalogue includes:

said processor identifying mutations as one of: tandem duplications, deletions, inversions or translocations and grouping mutations identified as tandem duplications, deletions or inversions by size, and said processor identifying mutations as being clustered or non-clustered, and wherein the presence or absence of one or more of the rearrangement signatures is associated with said type of cancer or a response to said particular cancer therapy.

16. The method of claim 15, further comprising:

determining, by said processor, the contribution of a second rearrangement signature to the rearrangement catalogue, the second rearrangement signature characterized by a presence of non-clustered tandem duplications greater than 100kb in length, the determining comprising computing the measure of similarity between the rearrangement mutations in said rearrangement catalogue and the second rearrangement signature;

determining that the second rearrangement signature characterized by the presence of non-clustered tandem duplications greater than 100kb in length is present in the DNA sample by determining if the number or proportion of rearrangements in the rearrangement catalogue which are determined to be associated with the second rearrangement signature characterized by the presence of non-clustered tandem duplications greater than 100kb in length exceeds a predetermined threshold;

selecting the subject for treatment with a particular cancer therapy for subjects whose cancer exhibit HRD when it is determined that the rearrangement signature characterized by the presence of non-clustered tandem duplications greater than 100kb in length is present in the DNA sample; and administering the particular cancer therapy to the subject.

17. The method of claim 15, wherein the cancer is breast cancer.

\* \* \* \* \*

UNITED STATES PATENT AND TRADEMARK OFFICE
CERTIFICATE OF CORRECTION

PATENT NO. : 11,929,144 B2
APPLICATION NO. : 16/096803
DATED : March 12, 2024
INVENTOR(S) : Serena Nik-Zainal et al.

It is certified that error appears in the above-identified patent and that said Letters Patent is hereby corrected as shown below:

In the Claims

At Column 15, Claim 4, Line 16:
"map (BAMS) files of"
Should read:
--map (BAM) files of--

Signed and Sealed this
Thirtieth Day of April, 2024

Katherine Kelly Vidal
*Director of the United States Patent and Trademark Office*